United States Patent [19]

Grant

[11] Patent Number: 4,650,302

[45] Date of Patent: Mar. 17, 1987

[54] INTERFEROMETRIC EYE TEST METHOD AND APPARATUS

[76] Inventor: Ralph M. Grant, 4480 Sheldon Rd., Rochester, Mich. 48063

[21] Appl. No.: 691,706

[22] Filed: Jan. 15, 1985

[51] Int. Cl.⁴ .......................... A61B 3/14; A61B 3/10
[52] U.S. Cl. ..................................... 351/206; 354/62; 351/211
[58] Field of Search .................. 351/206, 211; 354/62

[56] References Cited

U.S. PATENT DOCUMENTS 4,402,601  9/1983  Riva ............................... 351/221 X Primary Examiner—Rodney B. Bovernick
Attorney, Agent, or Firm—Krass & Young

[57] ABSTRACT

For purposes of eye examination, a method is provided for determining the presence or absence of structural anomaly in the retina. In this method, the surface of the retina (under zero stress or any one of a selected variety of stress conditions to produce deformation) is illuminated with coherent light and separate exposures or interferograms are made using the reflected light and recorded either photographically or electronically such as by storage or display via the cathode of a television image tube. The exposure may either be holographic, in which case the interferogram is produced by using a reference beam of light derived from the same source that illuminates the object surface, or shearographic, in which case two focused images of the retinal surface section are formed on a photosensitive medium, displaced with respect to one another and overlapping one another. The resultant hologram or shearogram is processed in conventional manner to derive an image of the object surface containing fringes arrayed as a function of the deformation of the surface between the several exposures. These fringes are analyzed to detect anomalous fringe families related to deformation that signifies structural anomaly in the retina.

12 Claims, 7 Drawing Figures

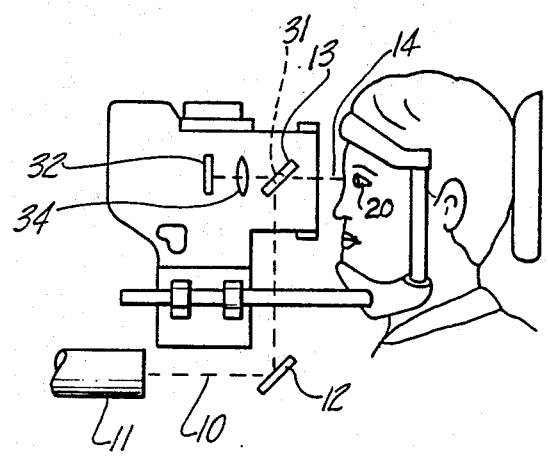
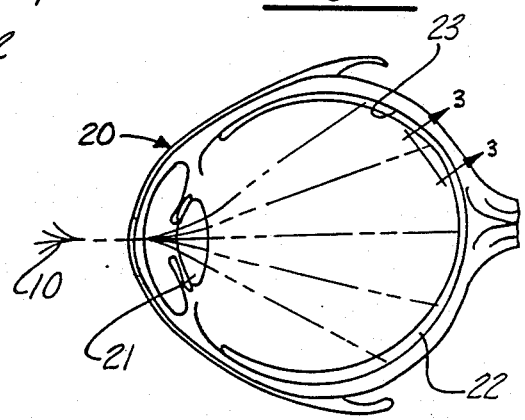
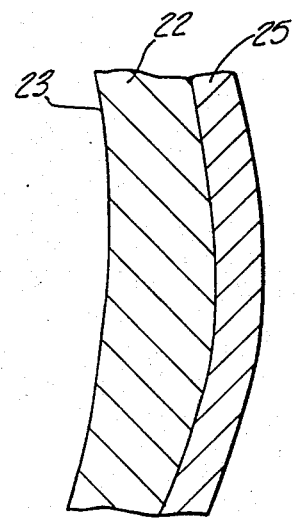
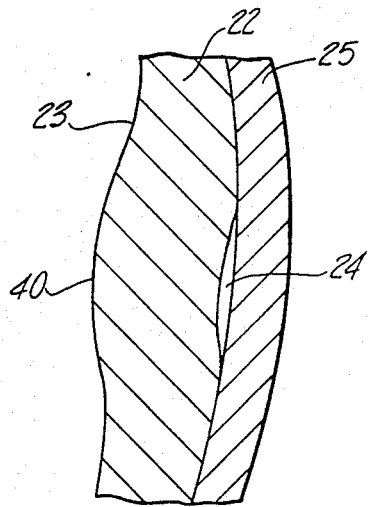
Fig-1
Fig-2
Fig-3A
Fig-3B

INTERFEROMETRIC EYE TEST METHOD AND APPARATUS

FIELD OF THE INVENTION

This invention relates to ophthalmic test apparatus and methods of eye examination employing interferometric holography or shearography for detecting the presence of structural anomalies or defects in the retina.

PRIOR ART

Apparatus employing coherent light for viewing the interior of the eye and measuring intraocular phenomena or recording reflected holographic images are known, for example, as described in U.S. Pat. Nos. 3,460,887 and 4,402,601.

Double exposure holography for general purposes is also known. Double exposure holography is a method of analyzing the deformation of an object surface between the times of the two exposures involving forming a first hologram on a photosensitive medium by exposing the medium to an object beam of coherent light reflected from the object surface and a reference beam of coherent light derived from the same source used to illuminate the object. If the photosensitive medium were processed following the formation of this first exposure to form a hologram and then illuminated with a reconstructing beam of coherent light comparable to the reference beam used during the formation of the hologram, an image of the object surface would be reconstructed. When a second exposure of the object surface is made before the hologram is developed, the reconstructed image of the object surface will contain fringe families arrayed as a function of the deformation of the surface between the two exposures because of the interference between the two holograms. This highly sensitive technique for detecting surface deformation can be used for nondestructive testing by stressing the object, as by mechanically loading, heating, or by using variations in normal intraocular pressing during the period between the two exposures. The fringe families will then reveal the deformation of the surface resulting from the stress and can be used to detect defects or structural anomalies in the test object which influence the surface deformation. Subsurface voids or discontinuities in structural members can be detected in this way.

Double exposure interferometric techniques involving the formation of two interferograms on the same light sensitive medium are similar to double exposure holographic interferometry but present various advantages and disadvantages compared to that technique. Double exposure techniques include shearography as disclosed in U.S. Pat. No 4,139,302 and speckle interferometry as disclosed in U.S. Pat. No. 3,816,649.

In the field of eye examination, the art has lacked means for examining the retina for the presence or absence of structural anomaly such as intermembrane separation, subsurface voids and discontinuities in the retina.

Accordingly, it is an object of this invention to provide a method and apparatus means employing interferometry for examining the retina of the eye for the presence or absence of structural anomaly in the retina.

This object and other objects, features and advantages will be seen from the following summary and detailed description of the invention.

SUMMARY AND DETAILED DESCRIPTION OF THE INVENTION

The present invention, in a method for the examination of the retina, broadly involves the formation of double exposure interferograms of the coherently illuminated retinal surface, with the exposures being taken with differential stress, either ambient stress or stress applied to the eye, e.g. before, during, and after ambient or applied stress. The successive exposures are such as to measure variations in strain as a result of variations in stress or displacement gradients of points on the retinal surface relative to one another. Each exposure of the interferogram represents an interferogram itself, produced by focusing a pair of images or the coherently illuminated surface on a photosensitive medium with a slight displacement of one image relative to the other, so that the images overlap through the major portion of their areas, but are not coincident. This will result in a slightly blurred image being recorded on the photosensitive medium with a superimposed interference pattern. The two exposures are made coincident with one another so that if the eye were not stressed between the two exposures, or were stressed but without a resultant retinal displacement gradient change, e.g. due to the presence of retinal anomaly, the two identical interferograms would appear as one image pattern. On the other hand, the two interference patterns recorded on the photosensitive medium during the double exposure, one before and one after stressing the eye will themselves interfere to form a multiple interference pattern. This multiple interference pattern, along with a slightly blurred but clearly recognizable image of the retinal structure appears on the photosensitive medium, the image being reproduced from the medium by any suitable means such as photography or video recording and/or display. In the description that follows, particular emphasis will be placed on the shearographic technique for purposes of producing the desired multiple interference pattern according to the invention. The invention, however, contemplates use of other equivalent techniques for this purpose such as double exposure holographic interferometry.

The invention in one preferred embodiment relates to a method of eye examination for detecting structural anomaly in the retina, comprising the steps of:

A. with the retina in a first stress condition, illuminating the retina surface with coherent light;

B. with the retina in the first stress condition, forming a record of a first exposure on a photosensitive medium of coherent light reflected from the retinal surface;

C. allowing the stress condition of the retina to change by an incremental amount to create a second stress condition;

D. with the retina in said second stress condition, forming a record of a second exposure on the photosensitive medium of coherent light reflected from the retinal surface, the reflected light recorded on the photosensitive medium during steps B and D being focused in such a way as to provide a pair of images corresponding to the retinal surface that are slightly displaced and mutually overlapping on the photosensitive medium;

E. using the records of the first and second exposures to form an interference pattern on the photosensitive medium as a function of a component of the strain or displacement gradient or of deformation of the retinal surface corresponding to the difference between the first and second exposure; and F. analyzing the interference pattern for the presence or absence of anomalous fringes characteristic of retinal anomaly. According to the invention, the change in stress condtion of the retina can be achieved in any suitable way such as by allowing the relina to undergo ambient deformation over time due to dynamic changes, naturally or externally caused, in the intraocular temperature and pressure.

In preferred aspects, one stress condition is a zero stress condition and the other stress condition is produced by application of digital pressure means or digital cooling means which may be progressively changing upon the eye.

In another preferred aspect, the change in stress condition is achieved by subjecting the eye to an ambient low temperature change and thereafter allowing the eye to regain its normal temperature. The reflective light recorded on the photosensitive medium during each of the exposures preferably is focused by shearographic lens means. The photosensitive medium preferably comprises a photographic film or the cathode of a television camera. Preferably a record of an interferometric image corresponding to the retinal structure with superimposed interference fringes is obtained by electronic storage, or by reading out the cathode onto a visual display device.

In still another preferred embodiment the invention concerns a method of eye examination for detecting structural in the retina comprising the steps of:

A. illuminatint the retinal surface with coherent light;
B. subjecting the illuminated retina to progressively varying stress conditions; and
C. for each of the selected changes in stress condition of the retina, forming a holographic or shearographic record of exposures on photosensitive media of coherent light reflected from the retinal surface, and as a preferred option,
D. analyzing exposure images of the record for the presence of any interferometric fringe pattens that are characteristic of structural anomaly in the retina. For the formation of a holographic interferogram, the photosensitive medium during each of the exposures is illuminated with a reference beam of light coherent with the light used to illuminate the retina. In this embodiment using multiple exposures corresponding to the progressive stress points, a progressive displacement gradient or deformation is achieved by subjecting the retina to discrete, relatively small pressure changes; or by subjecting the retina to a single major stress change and then taking a series of quick, successive exposures as the retina undergoes creep deformation in response to the major stress change or abrupt release thereof; or by subjecting the retina to a large ambient temperature change such as a temperature decrease and then taking a series of successive exposures as the retina progressively responds, during or after the large temperature change.

Other objects, advantages and applications of the invention will be seen from the following detailed description of preferred embodiments of the invention. The description makes reference to the accompanying drawings, in which:

FIG. 1 is a representation of apparatus for examination of the retina according to the invention;

FIG. 2 is a schematic representation of the eye illustrating illumination of the retina by incident coherent light;

FIGS. 3a and 3b are enlarged sectional views of the unstressed retina and the stressed retina, respectively, taken on line 3—3 of FIG. 2;

Figure 4A:
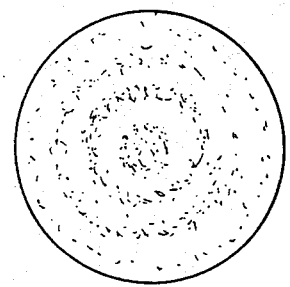
FIGS. 4a and 4b represent interferogram images of the retinal surface shown in FIGS. 3a (without stress) and 3b (with stress)

The apparatus illustrated in FIG. 1 for eye examination is adapted to analyze and record the strain pattern on the surface of the retina of the eye as the result of controlled stress imposed on the eye by way of altering the ambient pressure or temperature such that a measurable, reversible, non-invasive retinal displacement gradient or deformation is achieved. As shown, a coherent light beam 10 is directed from a laser 11 by way of a mirror 12 and a segmented reflection mirror 13 on an incident path 14 centrally into the eye 20 of a patient. The beam 10 then passes through the lens 21 (FIG. 2) and is diffused upon the retina 22. The beam is reflected from the retinal surface 23 outwardly from the eye on a line coinciding with the incident path 14. The collection system for the reflected beam comprises an optically transparent segment 31 in the reflection mirror 13, and a photosensitive plate 32. The collection system also includes interferometric lens means for projecting the reflected beam onto the photosensitive plate 32 which lens means preferably is a dual image projecting or focusing means such as a shearographic lens or shearing lens (FIG. 5) of the type described in U.S. Pat. No. 4,139,302. The photosensitive plate 32 preferably is a photographic plate or film for photographic recording of the image produced or, for electronic recording, the cathode of a television imaging tube such as a Vidicon or a rectangular photosensitive semi-conductor array.

The shearing lens (FIG. 5) consists of two parts. One part is a conventional double convex camera lens 34. A wedge 35 of optical glass covers one half of the lens. The uncovered half of the lens acts to focus light from the illuminated surface 23 onto the plate 32 in a conventional manner. For example, light from a point A on the surface 23 is focused on a point A' on the photosensitive medium 32 and light from a point B from the object surface 20 is focused at a point B'.

Light passing through the wedge 35 from the surface 23 is also focused on the plate 32 by the lens 34 to form an image of the surface 23 on the plate 32, but the image produced is shifted slightly with respect to the image produced by light passing through the uncovered lens section. For example, light reflected from the point A on the surface is focused at point A" on the photographic surface 32. It is thus not coincident with light from point A passing through the lens section 34, but rather reaches the point B'.

Figure 5:
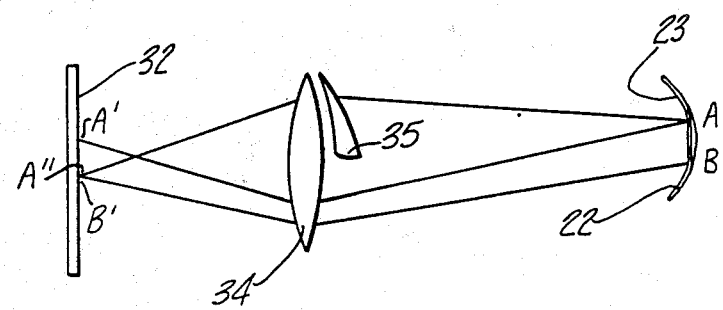
FIG. 5 is a schematic representation of an interferometric lens system for processing an interferogram.

Thus through use of the shearing lens, lights from points A and B on the surface 23 interfere with one another at the point A" which coincides with the point B' as in FIG. 5. Likewise the two images focused on the photographic medium 32 by the covered and uncovered lens sections interfere with one another in their overlapping regions. The shift produced by the wedge section 35 is preferably relatively slight compared to the overall dimension of the focused image.

Therefore, if the photosensitive plate were to be developed or displayed, a slightly blurred image of the surface 23 would be visible as in FIG. 4a, much like an image that is observed when an object photographed with a conventional camera moves during the exposure.

The blurred image would have an interference pattern superimposed on its surface resulting from a coherent interference from the two sheared images of the object. This interference pattern would be uniform both in frequency and in amplitude. Other optical elements capable of producing the shearing overlapping images could be employed as alternatives to the lenses 34, 35.

Following the recording of this first image on the photosensitive plate 32, and without shifting the plate or developing the image recorded thereon, the eye is stressed. Preferably this is done by utilizing digital pressure on the eye as with a pressure probe or by taking advantage in variations in the intraocular pressure which occurs due to the heart beating. The pressure may be increased or decreased relative to that of the first exposure. Then the laser 11 is turned on and another exposure is made on the photosensitive plate 32 of the illuminated retinal surface 23.

Suppose that the pressure change resulted in no strain on the surface 23. The photosensitive medium 32 would then have been exposed to two identical sheared images and upon development of the plate 32 a slightly blurred image of the surface 23 with an irregular pattern of equal frequency equal amplitude fringe lines would be observed.

Suppose further that the change in pressure resulted in some uniform change in position of the surface 23 of the object relative to the photosensitive medium; for example, a slight shift toward the medium or a slight shift laterally from the medium. In this event a second blurred image of the object would be recorded on the photographic plate along with an interference pattern resulting from the interference of the first set of interference fringes with the set resulting from this second blurred image. The two interference patterns would interfere with one another producing an overall interference pattern. Because of the uniform movement of the object of this pattern would be regular over the entire object surface. When the medium was developed a blurred image of the object would be seen and the regular interference pattern would be largely invisible because of its fine size and the fact that the regular amplitude, regularly spaced fringes would result in a uniform darkness level over the entire image.

Suppose however, as is the practical case, that the change in pressure produced an irregular strain over the object surface 23 as in FIG. 3b. For example, if a void, separation or detachment 24 existed at the retinal wall between the retina and the pigment epithelium or the choroid 25 at one point in close proximity to the surface 23, an increase in the ambient pressure might cause a relatively large deflection of that point relative to the balance of the retina. In that event, the interference pattern produced on the photosensitive plate as a result of interference of the two patterns produced during the first and second exposures, would be irregular. The frequency of the fringes would vary as a function of the displacement gradient or strain at each point on the object's surface between the two exposures.

Figure 4B:
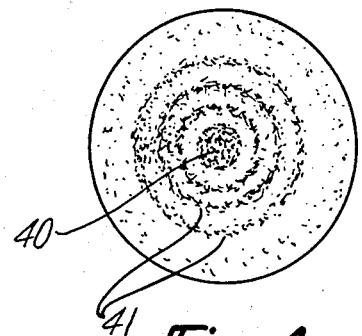

The resulting fringe pattern would have rings of alternating high frequency and low frequency fringes surrounding points of anomalous strain. FIG. 4b is an enlarged view of a small section of such a resulting interferogram. Assume that the point 40 has undergone an anomalous strain change. Rings or contours of constant displacement gradients of fringes 41 would surround this point.

The fringe families produced in the final image of the illuminated retinal surface differ somewhat in holography and shearography. In holography, the fringe lines are arrayed as a function of contours of constant displacement while in shearography the fringe lines are contoured as a function of loci of constant in-plane shear strain on the retina.

While preferred embodiments of the invention had been illustrated and described in detail, it will be apparent that various changes may be made in the preferred embodiments without departing from the scope or spirit of the invention. For example, although the invention has been illustrated and described with reference to changes in the stress condition of the retina brought about by changes in ambient pressure, the stress conditions of the retina may also be varied by ambient temperature changes. Specifically as mentioned, the retina may be subjected to a large ambient temperature change, whereafter multiple exposures may be taken of the object at successive times following the ambient temperature change. For example, the retina may be chilled by controlled application to the eye of a digital probe chilled with freon and then allowed to regain heat in a room temperature environment, whereafter successive exposures may be taken as the temperature of the eye moves progressively back toward room temperature.

I claim:

1. A method of eye examination for detecting structural anomaly in the retina, comprising the steps of:
   A. with the retina in a first stress condition, illuminating the retinal surface with coherent light;
   B. with the retina in the first stress condition, forming a record of a first exposure on a photosensitive medium of coherent light reflected from said retinal surface;
   C. allowing the stress condition of the retina to change by an incremental amount to create a second stress condition;
   D. with the retina in said second stress condition, forming a record of a second exposure on said photosensitive medium of coherent light reflected from said retinal surface, the reflected light recorded on the photosensitive medium during steps B and D being focused in such a way as to provide a pair of images corresponding to the retinal surface that are slightly displaced and mutually overlapping on the photosensitive medium;
   E. using the records of said first and second exposures to form an interference pattern on said photosensitive medium as a function of the change in said retinal surface corresponding to said first and second exposures; and
   F. analyzing said interference pattern for the presence or absence of anomalous fringes characteristic of retinal anomaly.

2. A method according to claim 1 wherein said incremental change in stress condition is achieved by variation in the intraocular pressure.

3. A method according to claim 1 wherein one stress condition is a zero stress condition and the other stress condition is produced by application of pressure upon the eye.

4. A method according to claim 1 wherein the change in stress condition is achieved by application of progressively changing pressure upon the eye.

5. A method according to claim 1 wherein the change in stress condition is achieved by application of digital cooling means upon the eye.

6. A method according to claim 5 wherein the change in stress condition is achieved by subjecting the eye to an ambient low temperature change and thereafter allowing the eye to regain its normal temperature.

7. A method according to claim 1 wherein the reflective light recorded on the photosensitive medium during each of said exposures is focused by shearographic lens means.

8. A methd according to claim 1 wherein the photosensitive medium comprises a cathode of a television camera and a record of an interferometric image corresponding to the retinal structure with superimposed interference fringes is obtained by electronic storage or by reading out the cathode onto a visual display device.

9. A method according to claim 1 wherein the photosensitive medium comprises a photographic film.

10. A method of eye examination for detecting structural anomaly in the retina comprising the steps of:
A. illuminating the retinal surface with coherent light;
B. subjecting the illuminated retina to progressively varying stress conditions; and
C. for each of selected changes in stress condition of the retina, forming a holographic or shearographic record of exposures on photosensitive media of coherent light reflected from the retinal surface.

11. A method according to claim 10 further comprising the step of:
D. analyzing exposure images of said record for the presence of any interferometric fringe patterns that are characteristic of structural anomaly in the retina.

12. A method according to claim 10 wherein during each of said expposures the photosensitive medium is illuminated with a reference beam of light coherent with the light used to illuminate the retina to form a multiple exposure holographic interferogram.

* * * * *

UNITED STATES PATENT AND TRADEMARK OFFICE
CERTIFICATE OF CORRECTION

PATENT NO. : 4,650,302

DATED : March 17, 1987

INVENTOR(S) : Ralph M. Grant

It is certified that error appears in the above-identified patent and that said Letters Patent is hereby corrected as shown below:

Column 2, line 15 "or" should be --of--.

Column 3, line 5 "relina" should be --retina--.

Column 3. line 30 "structural in the retina" should be --structural anamaly in the retina--.

Column 3, line 31 "illuminatint" should be --illuminating--.

Column 8, line 18 "expposures" should be --exposures--.

Signed and Sealed this

Eighth Day of September, 1987

Attest:

DONALD J. QUIGG

Attesting Officer    Commissioner of Patents and Trademarks